(12) United States Patent
Christiansen et al.

(10) Patent No.: US 9,409,844 B2
(45) Date of Patent: *Aug. 9, 2016

(54) MIXTURE OF DIFFERENT ASYMMETRICAL BISOPHOSPHITES AND USE THEREOF AS A CATALYST MIXTURE IN HYDROFORMYLATION

(71) Applicant: EVONIK DEGUSSA GMBH, Essen (DE)

(72) Inventors: Andrea Christiansen, Rostock (DE); Robert Franke, Marl (DE); Dirk Fridag, Haltern am See (DE); Dieter Hess, Marl (DE); Katrin Marie Dyballa, Recklinghausen (DE); Bernd Hannebauer, Muehlheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/434,827

(22) PCT Filed: Sep. 27, 2013

(86) PCT No.: PCT/EP2013/070238
§ 371 (c)(1),
(2) Date: Apr. 10, 2015

(87) PCT Pub. No.: WO2014/056737
PCT Pub. Date: Apr. 17, 2014

(65) Prior Publication Data
US 2015/0266008 A1    Sep. 24, 2015

(30) Foreign Application Priority Data

Oct. 12, 2012 (DE) .......... 10 2012 218 625
Oct. 12, 2012 (DE) .......... 10 2012 218 627
Oct. 12, 2012 (DE) .......... 10 2012 218 629
Oct. 12, 2012 (DE) .......... 10 2012 218 630

(51) Int. Cl.
| | |
|---|---|
| C07F 9/30 | (2006.01) |
| C07C 45/50 | (2006.01) |
| B01J 31/18 | (2006.01) |
| C07F 9/6574 | (2006.01) |
| B01J 31/02 | (2006.01) |
| B01J 19/24 | (2006.01) |
| C07C 67/38 | (2006.01) |
| C07F 9/6571 | (2006.01) |
| C07F 15/00 | (2006.01) |
| C07F 9/6568 | (2006.01) |

(52) U.S. Cl.
CPC .......... *C07C 45/505* (2013.01); *B01J 19/24* (2013.01); *B01J 31/0209* (2013.01); *B01J 31/0237* (2013.01); *B01J 31/0271* (2013.01); *B01J 31/185* (2013.01); *C07C 45/50* (2013.01); *C07C 67/38* (2013.01); *C07F 9/6571* (2013.01); *C07F 9/65746* (2013.01); *C07F 15/0073* (2013.01); *B01J 2219/24* (2013.01); *B01J 2231/321* (2013.01); *B01J 2531/822* (2013.01); *C07F 9/65683* (2013.01); *C07F 9/65685* (2013.01)

(58) Field of Classification Search
USPC .......................................... 568/12, 14
See application file for complete search history.

(56) References Cited

U.S. PATENT DOCUMENTS

| | | | |
|---|---|---|---|
| 4,067,890 A | 1/1978 | Rutledge | |
| 4,668,651 A * | 5/1987 | Billig ............ | B01J 31/185 502/158 |
| 4,769,498 A | 9/1988 | Billig et al. | |
| 5,288,918 A | 2/1994 | Maher et al. | |
| 8,461,394 B2 | 6/2013 | Lueken et al. | |
| 8,884,070 B2 | 11/2014 | Franke et al. | |
| 2003/0195368 A1 | 10/2003 | Rottger et al. | |
| 2015/0018576 A1 | 1/2015 | Baumgarten et al. | |

FOREIGN PATENT DOCUMENTS

| | | |
|---|---|---|
| DE | 25 36 870 A1 | 3/1976 |
| EP | 1 294 731 B1 | 2/2004 |
| EP | 2 003 138 A1 | 12/2008 |
| WO | WO 2014/056733 A1 | 4/2014 |
| WO | WO 2014/056735 A1 | 4/2014 |
| WO | WO 2014/056736 A1 | 4/2014 |

OTHER PUBLICATIONS

U.S. Appl. No. 14/435,007, filed Apr. 10, 2015, Christiansen, et al.
U.S. Appl. No. 14/434,988, filed Apr. 10, 2015, Christiansen, et al.
U.S. Appl. No. 14/434,879, filed Apr. 10, 2015, Christiansen, et al.
U.S. Appl. No. 14/435,052, filed Apr. 10, 2015, Fridag, et al.
U.S. Appl. No. 08/461,394, filed Jun. 11, 2013, Lueken, et al.
U.S. Appl. No. 14/380,647, filed Aug. 22, 2014, Baumgarten, et al.
U.S. Appl. No. 08/884,070, filed Nov. 11, 2014, Franke, et al.
International Search Report issued Jan. 7, 2014 in PCT/EP2013/070238.
Office Action issued May 31, 2013 in German Patent Application No. 10 2012 218 630.1.
Robert Franke, et al., "Applied Hydroformylation", Chemical Reviews, vol. 112, (2012), pp. 5675-5732.

* cited by examiner

*Primary Examiner* — Pancham Bakshi
(74) *Attorney, Agent, or Firm* — Oblon, McClelland, Maier & Neustadt, L.L.P

(57) ABSTRACT

The invention relates to a mixture of unsymmetric bisphosphites, to a process for preparation thereof, to the reaction thereof with metals to give mixtures comprising complexes of the bisphosphites and the metal, and to the use thereof as a catalytically active composition in hydroformylation reactions, and also to the hydroformylation reaction itself.

16 Claims, 1 Drawing Sheet

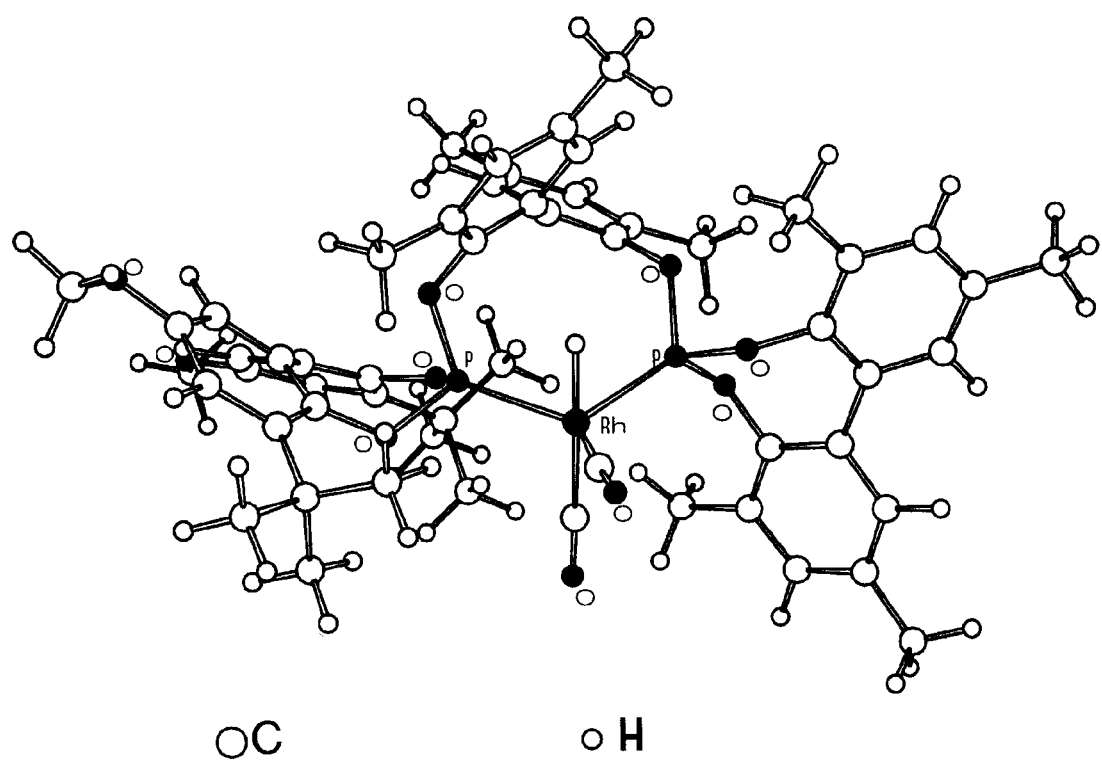

MIXTURE OF DIFFERENT ASYMMETRICAL BISOPHOSPHITES AND USE THEREOF AS A CATALYST MIXTURE IN HYDROFORMYLATION

The invention relates to a mixture of unsymmetric bisphosphites, to a process for preparation thereof, to the reaction thereof with metals to give mixtures comprising complexes of the bisphosphites and the metal, and to the use thereof as a catalytically active composition in hydroformylation reactions, and also to the hydroformylation reaction itself.

The reactions between olefin compounds, carbon monoxide and hydrogen in the presence of a catalyst to give the aldehydes with one carbon atom more is known as hydroformylation or the oxo process. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Catalytically active compositions based on rhodium-bisphosphite complexes are suitable for the hydroformylation of linear olefins having terminal and internal double bonds, forming predominantly terminally hydroformylated products. In contrast, branched olefins having internal double bonds are converted only to a small degree. When they coordinate to a transition metal site, these phosphites give rise to catalysts of enhanced activity, but the service life characteristics of these catalytically active compositions is unsatisfactory, one reason being the hydrolysis sensitivity of the phosphite ligands. The use of substituted bisaryldiols as starting materials for the phosphite ligands, as described in EP 0 214 622 or EP 0 472 071, achieved considerable improvements.

According to the literature, the catalytically active compositions of these ligands based on rhodium are exceptionally active in the hydroformylation of α-olefins. U.S. Pat. No. 4,668,651, U.S. Pat. No. 4,748,261 and U.S. Pat. No. 4,885,401 describe polyphosphite ligands with which α-olefins, but also 2-butene, can be converted with high n/i selectivity to the terminally hydroformylated products. Bidentate ligands of this type were also used for hydroformylation of butadiene (U.S. Pat. No. 5,312,996).

The bisphosphites disclosed in EP 1 294 731 have olefin conversions up to 98% in the hydroformylation of n-octene mixtures. However, n-selectivity for nonanal, which is likewise desired, is in need of improvement at 36.8% up to a maximum of 57.6%. This is all the more true in that the use of the catalytically active composition in industrial operations requires a service life measured in days rather than hours.

The literature discloses the synthesis of symmetric bisphosphites as disclosed since U.S. Pat. No. 4,769,498, and the use thereof in catalytically active, transition metal-containing compositions for hydroformylation of unsaturated compounds.

In U.S. Pat. No. 4,769,498, and also in U.S. Pat. No. 5,723,641, preferably symmetric bisphosphites are prepared and used as ligands for hydroformylation. The symmetric bisphosphite ligands used in the hydroformylation are prepared at low temperatures. Compliance with these low temperatures is absolutely necessary, since higher temperatures, according to these US documents, would lead to rearrangements and ultimately to unsymmetric bisphosphites, which is not wanted here.

The bisphosphites disclosed in U.S. Pat. No. 5,288,918 in column 8 under the general formula (V) are symmetric bisphosphites. The bisphosphite is symmetric even when $X^1$ and $X^2$ are different radicals, as is the case in the table in column 11 for Ref. No. 2 and 3.

Normally, in the prior art, ligands of maximum purity are used in the hydroformylation reaction, since the other isomer in each case exerts strong adverse effects on the overall performance of the system. In general, the unsymmetric isomer would be present as a secondary component, since exclusively symmetric ligands are used in the hydroformylation.

WO 2007/149143 describes a mixture of two monophosphites which is used as an antioxidant for polymer resins.

The use of two unsymmetric bisphosphites in hydroformylation has not been described to date.

The technical object of the present invention is the provision of novel ligands which do not have the above-detailed disadvantages from the prior art in the hydroformylation of unsaturated compounds, but instead have the following properties:

1.) a high activity, and

2.) a high n-regioselectivity in relation to the hydroformylation and

3.) a high service life.

A high service life means that the hydroformylation-active composition comprising the ligands in addition to further components has a low tendency to degradation of these ligands and/or to decomposition of these ligands to hydroformylation-inhibiting components, for example the "poisoning phosphites".

The object is achieved by a mixture of unsymmetric bisphosphites comprising the compounds (Ia') and (Ia''):

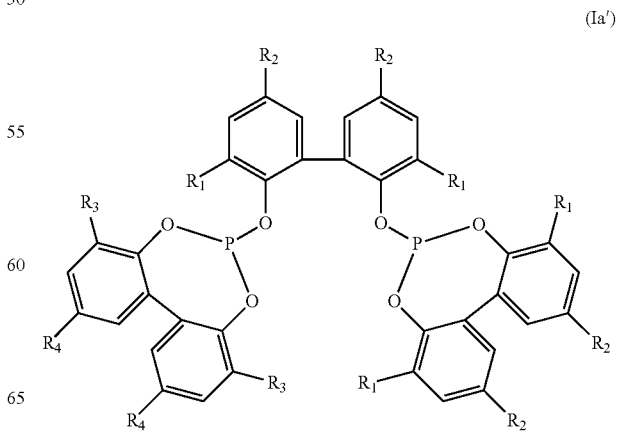

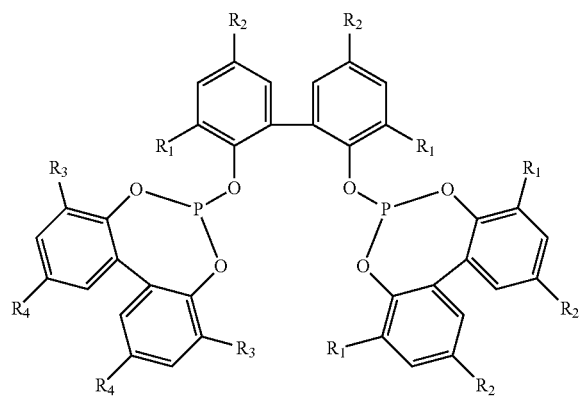

(Ia″)

where
R1 is selected from -Me, -tBu, —OMe;
R2 is selected from -Me, -tBu, —OMe;
R3 is selected from -Me, -tBu, —OMe;
R4 is selected from -Me, -tBu, —OMe;
and P can enter into further bonds,
and the compounds (Ia') and (Ia″) are not identical.

Each of Ia' and Ia″ is unsymmetric. Thus, a mixture of two different unsymmetric bisphosphites is present. "Unsymmetric" means that, if R1 is the same as R3, R2 cannot at the same time be the same as R4. Or if R2 is the same as R4, R1 cannot at the same time be R3.

In one embodiment, the content of compound (Ia') is within a range from 99.5 to 0.5 mol %, and the content of compound (Ia″) within a range from 0.5 to 99.5 mol %.

The two compounds (Ia') and (Ia″) add up to 100 mol %.

By way of example for the various R radicals, the compounds (1Ia') and (1Ia″) are summarized in Table 1 below.

TABLE 1

| | Isomer | R1 | R2 | R3 | R4 |
|---|---|---|---|---|---|
| (1Ia') | (Ia') | —Me | —Me | —tBu | —OMe |
| (1Ia″) | (Ia″) | —tBu | —OMe | —Me | —Me |

In one embodiment, the mixture comprises compounds Ib' and Ib″:

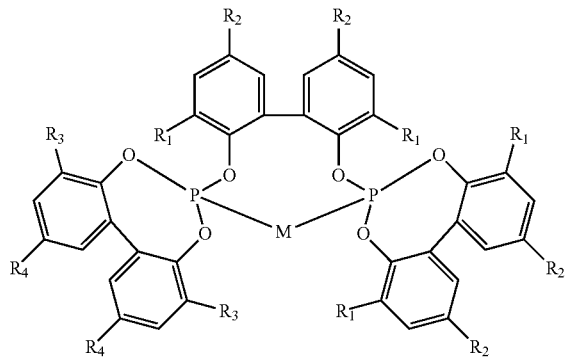

(Ib')

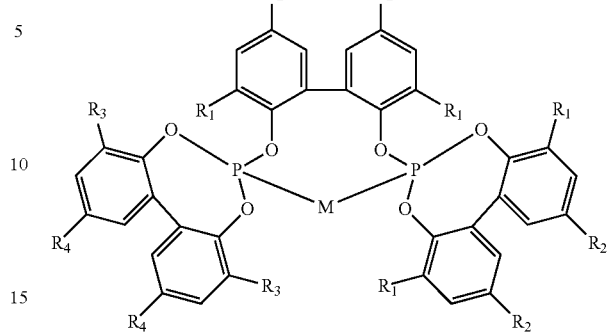

(Ib″)

where M is selected from Fe, Ru, Os, Co, Rh, Ir, Ni, Pd, Pt, and M can enter into additional bonds,
and the compounds (Ib') and (Ib″) are not identical.

In one embodiment, the content of compound (Ib') is within a range from 99.5 to 0.5 mol %, and the content of compound (Ib″) within a range from 0.5 to 99.5 mol %.

The two compounds (Ib') and (Ib″) add up to 100 mol %.

In one embodiment, the mixture comprises compounds Ic' and Ic″:

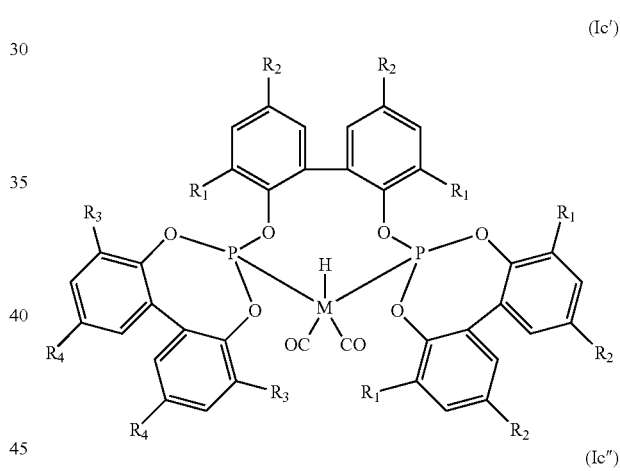

(Ic')

(Ic″)

where M is selected from Fe, Ru, Os, Co, Rh, Ir, Ni, Pd, Pt, and the compounds (Ic') and (Ic″) are not identical.

In one embodiment, the content of compound (Ic') is within a range from 99.5 to 0.5 mol %, and the content of compound (Ic″) within a range from 0.5 to 99.5 mol %.

The two compounds (Ic') and (Ic") add up to 100 mol %.

In one embodiment, the mixture comprises at least one compound (Ia') or (Ia") not bonded to M.

In one embodiment, M is Rh.

In one embodiment, R1 is -Me, and R3 is not -Me.

In one embodiment, R2 is -Me, and R4 is not -Me.

In one embodiment, R1 and R2 are each -Me.

In one embodiment, R1 is -tBu, and R3 is not -tBu.

In one embodiment, R2 is —OMe, and R4 is not —OMe.

In a preferred embodiment, the bisphosphites have the structures (IIa') and (IIa"):

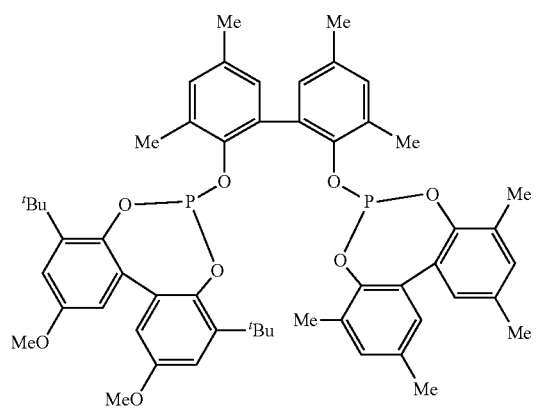

(IIa')

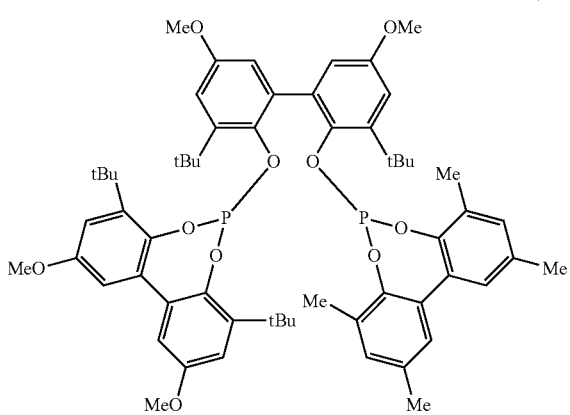

(IIa")

As well as the mixture, a composition comprising the latter is also claimed.

Composition comprising:
an above-described mixture,
a further component selected from: bases, organic amines, epoxides, buffer solutions, ion exchangers.

In a preferred embodiment, further components used are sterically hindered secondary amines.

It is also possible to use mixtures comprising two or more sterically hindered amines.

The composition comprises an above-described mixture including, in addition to the mixture, at least one amine having a 2,2,6,6-tetramethylpiperidine unit.

More particularly, in the process according to the invention, the amine having the formula (7), di-4-(2,2,6,6-tetramethylpiperidinyl) sebacate, is used with preference.

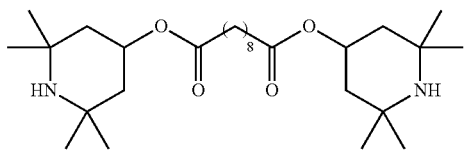

(7)

A particularly preferred metal in the inventive composition is rhodium.

As well as the mixture itself, the use thereof as a catalyst in a hydroformylation reaction of unsaturated compounds and mixtures thereof is also claimed.

Additionally claimed is a process for hydroformylating unsaturated compounds and mixtures thereof.

Process for hydroformylating unsaturated compounds and mixtures thereof using:
an above-described composition, and
a gas mixture comprising carbon monoxide and hydrogen.

In one variant of the process, the unsaturated compounds and mixtures thereof are selected from:
hydrocarbon mixtures from steamcracking plants;
hydrocarbon mixtures from catalytically operated cracking plants;
hydrocarbon mixtures from oligomerization operations;
hydrocarbon mixtures comprising polyunsaturated compounds;
unsaturated carboxylic acid derivatives.

The unsaturated compounds which are hydroformylated in the process according to the invention include hydrocarbon mixtures obtained in petrochemical processing plants. Examples of these include what are called $C_4$ cuts. Typical compositions of $C_4$ cuts from which the majority of the polyunsaturated hydrocarbons has been removed and which can be used in the process according to the invention are listed in Table 2 below (see DE 10 2008 002188).

TABLE 2

| Component | Steamcracking plant | | Steamcracking plant | | Catalytic cracking plant | |
|---|---|---|---|---|---|---|
| | $HCC_4$ | $HCC_4$/SHP | Raff. I | Raff. I/SHP | $CC_4$ | $CC_4$/SHP |
| isobutane [% by mass] | 1-4.5 | 1-4.5 | 1.5-8 | 1.5-8 | 37 | 37 |
| n-butane [% by mass] | 5-8 | 5-8 | 6-15 | 6-15 | 13 | 13 |
| E-2-butene [% by mass] | 18-21 | 18-21 | 7-10 | 7-10 | 12 | 12 |
| 1-butene [% by mass] | 35-45 | 35-45 | 15-35 | 15-35 | 12 | 12 |
| isobutene [% by mass] | 22-28 | 22-28 | 33-50 | 33-50 | 15 | 15 |
| Z-2-butene [% by mass] | 5-9 | 5-9 | 4-8 | 4-8 | 11 | 11 |
| 1,3-butadiene [ppm by mass] | 500-8000 | 0-50 | 50-8000 | 0-50 | <10000 | 0-50 |

Key:
$HCC_4$: typical of a $C_4$ mixture which is obtained from the $C_4$ cut from a steamcracking plant (high severity) after the hydrogenation of the 1,3-butadiene without additional moderation of the catalyst.
$HCC_4$/SHP: $HCC_4$ composition in which residues of 1,3-butadiene have been reduced further in a selective hydrogenation process/SHP.

Raff. I (raffinate I): typical of a $C_4$ mixture which is obtained from the $C_4$ cut from a steamcracking plant (high severity) after the removal of the 1,3-butadiene, for example by an NMP extractive rectification.

Raff. I/SHP: raff. I composition in which residues of 1,3-butadiene have been reduced further in a selective hydrogenation process/SHP.

$CC_4$: typical composition of a $C_4$ cut which is obtained from a catalytic cracking plant.

$CC_4$/SHP: composition of a $C_4$ cut in which residues of 1,3-butadiene have been reduced further in a selective hydrogenation process/SHP.

In one variant of the process, the unsaturated compound or mixture thereof has been selected from:
  hydrocarbon mixtures from steamcracking plants;
  hydrocarbon mixtures from catalytically operated cracking plants, for example FCC cracking plants;
  hydrocarbon mixtures from oligomerization operations in homogeneous phase and heterogeneous phases, for example the OCTOL, DIMERSOL, Fischer-Tropsch, Polygas, CatPoly, InAlk, Polynaphtha, Selectopol, MOGD, COD, EMOGAS, NExOCTANE or SHOP process;
  hydrocarbon mixtures comprising polyunsaturated compounds;
  unsaturated carboxylic acid derivatives.

In one variant of the process, the mixture includes unsaturated compounds having 2 to 30 carbon atoms.

In a particular variant of the process, the mixture includes unsaturated compounds having 2 to 8 carbon atoms.

In a further variant of the process, the mixture includes polyunsaturated hydrocarbons. In a particular embodiment, the mixture comprises butadiene.

The unsaturated compounds which are hydroformylated in the process according to the invention additionally include unsaturated carboxylic acid derivatives. In a particular embodiment, these unsaturated carboxylic acid derivatives are selected from fatty acid esters.

The process according to the invention is performed in different embodiments which are disclosed in detail in the examples.

The inventive polyphasic reaction mixture comprises, as well as a gas mixture consisting of carbon monoxide and hydrogen, at least one unsaturated compound as disclosed above, and comprises, as well as hydrocarbon mixtures which originate from steamcracking, catalytically operated cracking plants or oligomerization operations, or contain other sources of monounsaturated and/or polyunsaturated carbon compounds or unsaturated carboxylic acid derivatives, at least one hydroformylation product of these unsaturated compounds as detailed in the examples which follow, and the composition used in each case, as disclosed above.

FIG. 1 shows the calculated complex (Ic') where R1=Me, R2=Me, R3=tBu, R4=OMe and M=Rh.

The inventive complexes of the formulae (Ic') and (Ic") are formed in situ during the hydroformylation reaction.

In a particular embodiment of the invention, the complexes (Ic') and (Ic") are present alongside the unbound bisphosphite.

The hydridocarbonyl complex (Ic') with rhodium as the metal was characterized by means of theoretical calculations. The result is shown in FIG. 1 in the appendix.

The structure calculation was conducted with the BP86 functional and the def-SV(P) base set. The structure calculations for the model structures were effected with the Turbomole program package (R. Ahlrichs, M. Bar, M. Häser, H. Horn, C. Kölmel, Chem. Phys. Lett., 1989, 162, 16; TURBOMOLE V6.3 2011, a development of University of Karlsruhe and Forschungszentrum Karlsruhe GmbH, 1989-2007, TURBOMOLE GmbH, since 2007. http://www.turbomole.com) on the basis of density functional theory (DFT). The BP86 functional (S. H. Vosko, L. Wilk, M. Nusair, Can. J. Phys., 1980, 58, 1200; A. D. Becke, Phys. Rev. A, 1988, 38, 3098; J. Perdew, Phys. Rev. B, 1986, 33, 8822) and the def-SV(P) base set (A. Schafer, H. Horn and R. Ahlrichs, J. Chem. Phys., 1992, 97, 2571) were used.

Furthermore, a process for preparing an above-described mixture is also claimed.

Process for preparing a mixture as described above, comprising the process steps of:

a) oxidative coupling according to reaction scheme A:

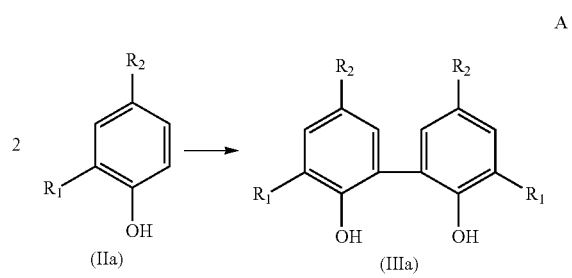

b) oxidative coupling according to reaction scheme B:

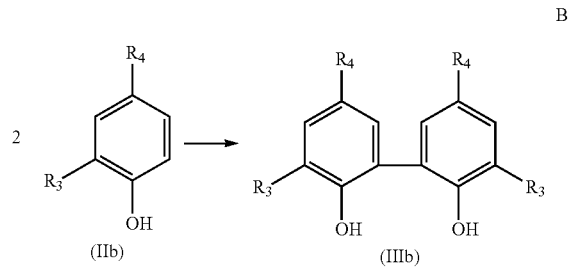

c) reaction of the product from a) with $PCl_3$ according to reaction scheme C:

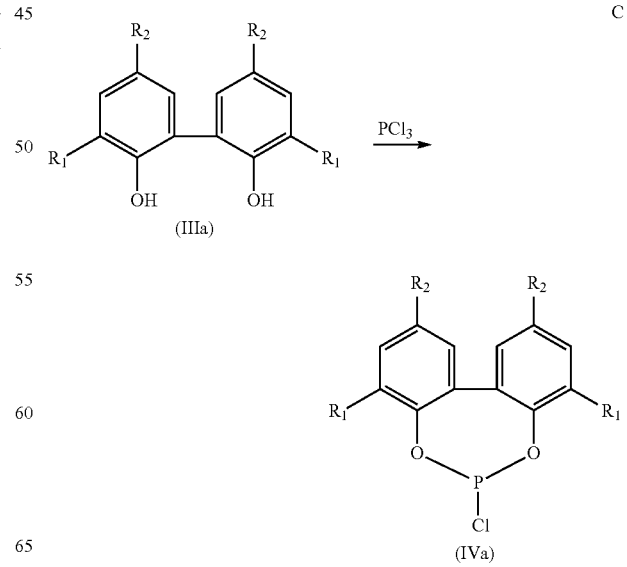

d) reaction of the product from b) with the product from c) to give a bisphosphite,
e) repetition of process steps a) to d), where the R1 to R4 radicals are selected such that they are not all identical to the first run,
f) mixing of the compounds from the first and second runs.

In one variant of the process, this additionally comprises the process step of
g) reaction with M to give (Ic') and (Ic"), where M is selected from Fe, Ru, Os, Co, Rh, Ir, Ni, Pd, Pt.

EXAMPLES

General Reaction Equation for Synthesis of Compound (1Ia')

Synthesis of 2,2'-bis(3,5-dimethylphenol) (3IIIa)

The biphenol (3IIIa) used as a precursor was prepared by the synthesis method which follows.

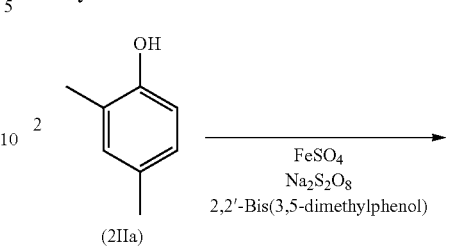

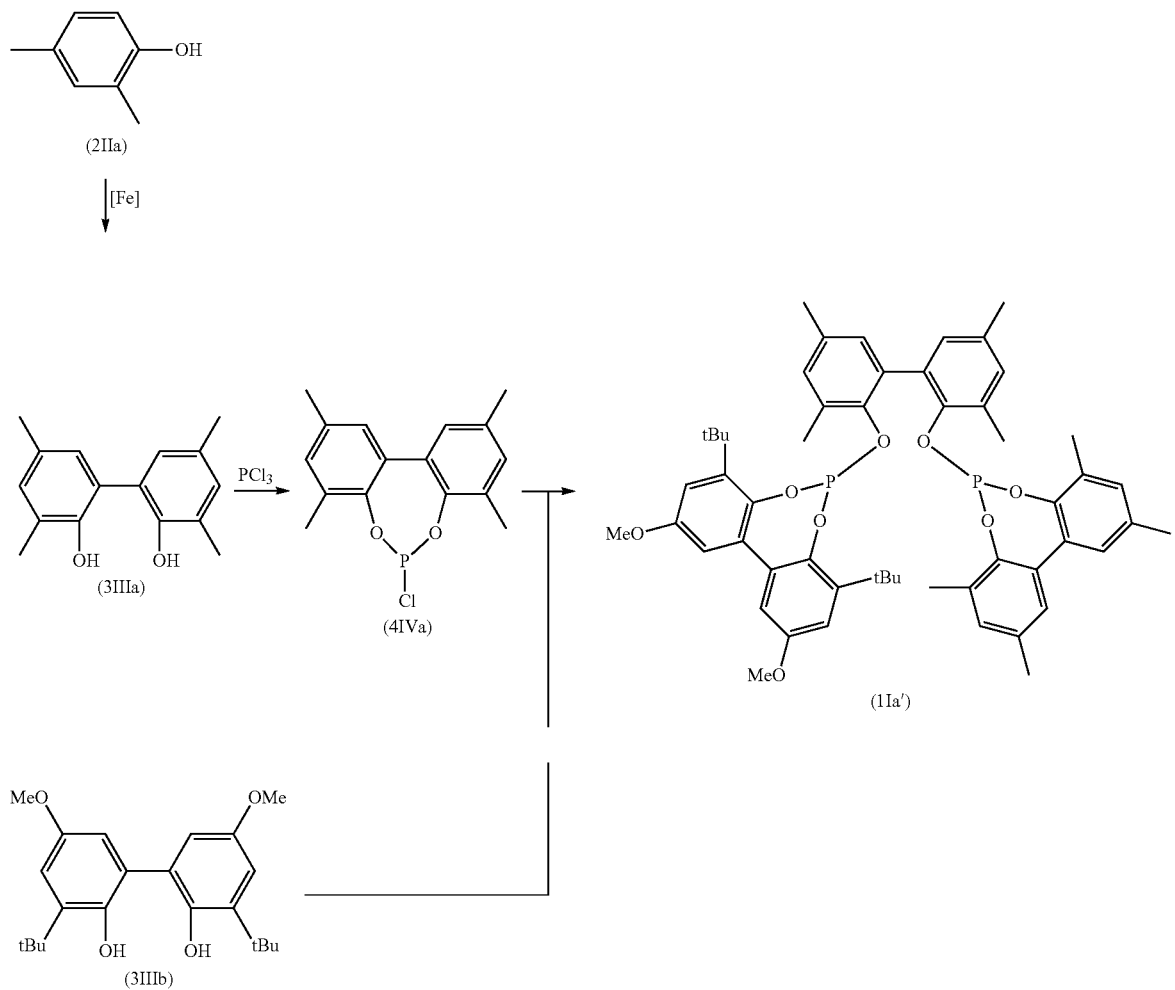

Abbreviations:
DM water=demineralized water
CPG=core-pulled precision glass
ACN=acetonitrile
EtOAc=ethyl acetate
acac=acetylacetonate
NEt₃=triethylamine
TIPB=1,2,4,5-tetraisopropylbenzene -continued

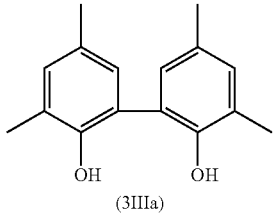

A 500 ml Schlenk with CPG stirrer, intermediate section and glass stirrer was initially charged with 1.42 g (0.005 mol) of iron(II) sulphate heptahydrate and 12.35 g (0.1 mol) of 2,4-dimethylphenol in 150 ml of DM water and 5 ml of cyclohexane, and the mixture was heated to 40° C.

In a 100 ml beaker, 25.36 g (0.146 mol) of sodium peroxodisulphate were dissolved in 80 ml of DM water. At the start of the reaction, a small portion of $Na_2S_2O_8$ solution was added to the phenol. Subsequently, a smaller portion of the solution was added every 10 min. After 30 min, the addition of $Na_2S_2O_8$ solution had ended.

After a reaction time of 5 h, 300 ml of cyclohexane and 200 ml of water were added to the reaction solution, which was left to stir for 20 min, then transferred while warm into a separating funnel.

The organic phase was removed and concentrated to dryness. The product (3IIIa) was obtained in 69% yield (10.6 g).

All the preparations which follow were conducted with standard Schlenk technology under protective gas. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts (δ) are reported in ppm. The $^{31}$P NMR signals were referenced according to: $SR_{31P}=SR_{1H}*$ $(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). By means of $^{31}$P NMR, the content of the ligands was determined.

Synthesis of 2,2'-bis(3,5-dimethylphenol)chlorophosphite (4IVa)

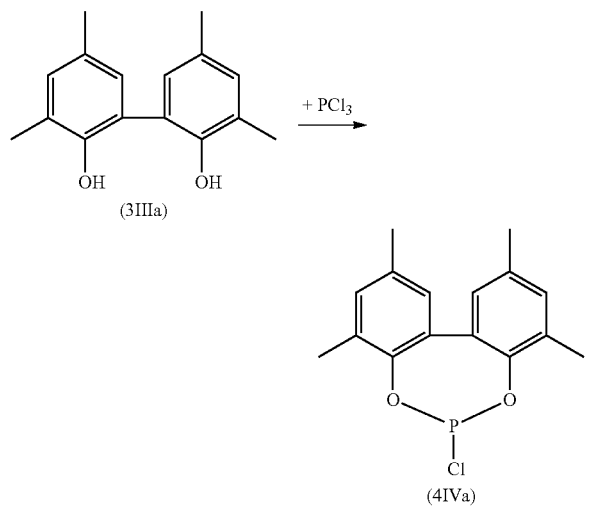

A secured 2 l Schlenk with magnetic stirrer was initially charged with 440 ml of phosphorus trichloride. 120 g of 2,2'-bis(3,5-dimethylphenol) were weighed into a second secured 1 l Schlenk and 500 ml of dried toluene were added while stirring. The biphenol-toluene suspension was metered into the phosphorus trichloride at 63° C. within 4 h. On completion of addition, the reaction mixture was stirred at temperature overnight. The next morning, the solution was concentrated while warm (45° C.), and the product was obtained in 96.5% yield (153 g). $^{31}$P NMR: 175.59 (94.8% 2,2'-bis(3,5-dimethylphenol)chlorophosphite), 4.4% various PCI compounds, 0.8% P—H compound.

Inventive Synthesis Variations for Preparation of the Pure Ligand (1Ia')

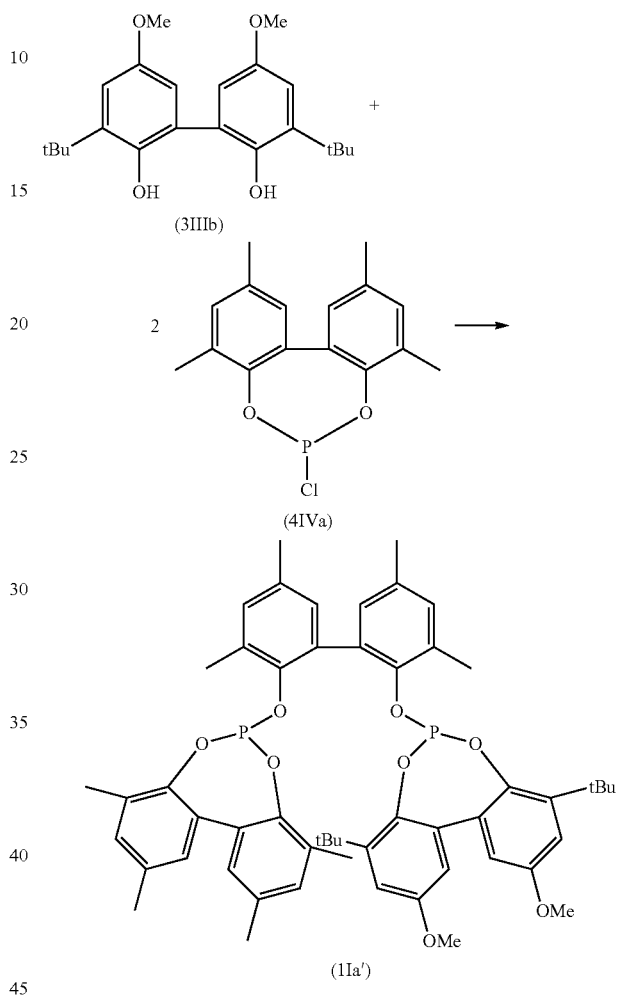

Variant 1: ACN/NEt$_3$

In a 1000 ml Schlenk, under protective gas, 38.75 g (0.121 mol) of 2,2'-bis(3,5-dimethylphenol)chlorophosphite were dissolved in 150 ml of degassed ACN and heated to 35° C. In a second Schlenk (500 ml), 20.1 g (0.056 mol) of 3,3'-di-tert-butyl-5,5'-dimethoxy-[1,1'-biphenyl]-2,2'-diol were dissolved in 150 ml of degassed ACN, and 40.9 ml of degassed triethylamine (0.29 mol) were added while stirring. Then the biphenol/triethylamine solution was slowly added dropwise to the chlorophosphite solution. After a further reaction time of 1 h, the reaction solution was stirred at 45° C. overnight.

These solids were stirred in degassed ACN at 75° C. for 1.5 h and removed with a frit and washed with warm ACN. Subsequently, the product was stirred in dried toluene at 35° C. for 1.5 h and removed with a frit. The target product was obtained as a white solid (33 g, 66%). $^{31}$P NMR (202.4 MHz, toluene-d$_8$): 142.5 and 140.9 (100%).

Variant 2: EtOAc/NEt$_3$

In a 100 ml Schlenk, under protective gas, 7.3 g (21.0 mmol) of 2,2'-bis(3,5-dimethylphenol)chlorophosphite were dissolved in 15 ml of degassed ethyl acetate and heated to 35° C. In a second Schlenk (100 ml), 3.9 g (9.5 mmol) of 3,3'-ditert-butyl-5,5'-dimethoxy-[1,1'-biphenyl]-2,2'-diol were dissolved in 7.0 ml of NEt$_3$. Subsequently, the biphenol/triethylamine solution was slowly added dropwise to the chlorophosphite solution within 20 minutes. The solution was stirred at 35° C. for a further hour and then at 45° C. overnight.

These solids were stirred in degassed ACN at 75° C. for 1.5 h and removed with a frit and washed with warm ACN. Subsequently, the product was stirred in dried toluene at 35° C. for 1.5 h and removed with a frit.

The target product was obtained as a white solid (5.0 g, 58%). $^{31}$P NMR (202.4 MHz, toluene-d$_8$): 142.5 and 140.9 (100%).

Variant 3: EtOAc/Pyridine

In a 250 ml Schlenk, under protective gas, 10.07 g (31.0 mmol) of 2,2'-bis(3,5-dimethylphenol)chlorophosphite were dissolved in 20 ml of degassed ethyl acetate and heated to 45° C. In a second Schlenk (50 ml), 5.54 g (15 mmol) of 3,3'-di-tert-butyl-5,5'-dimethoxy-[1,1'-biphenyl]-2,2'-diol were dissolved in 26 ml of ethyl acetate and 5.2 ml of degassed pyridine. Subsequently, the biphenol/pyridine solution was slowly added dropwise to the chlorophosphite solution within 30 minutes. The solution was stirred at 45° C. overnight.

The next day, the solution was filtered and the solids were washed with ACN. The target product was obtained as a white solid (4.2 g, 31%). $^{31}$P NMR (202.4 MHz, toluene-d$_8$): 142.2 and 141.1 (100%).

Variant 4: Performance of a Low-Temperature Experiment at −20° C.

In a 250 ml Schlenk, under protective gas, 8.0 g (0.025 mol) of 2,2'-bis(3,5-dimethylphenol)chlorophosphite were dissolved in 30 ml of degassed ACN and cooled to −20° C. In a second Schlenk (100 ml), 4.32 g (0.012 mol) of 3,3'-di-tert-butyl-5,5'-dimethoxy-[1,1'-biphenyl]-2,2'-diol were dissolved in 30 ml of degassed ACN, and 8.5 ml of degassed triethylamine were added while stirring. Then the biphenol/triethylamine solution was slowly added dropwise at −20° C. to the chlorophosphite solution. On completion of addition, stirring was continued at −20° C. for a further 4 hours. The reaction solution was stirred overnight at −10° C. until the next day. This procedure, reaction temperature at −20° C. through the day and at −10° C. overnight, was conducted repeatedly for 3 days. Thereafter, the reaction mixture was brought to RT within 3 hours.

Subsequently, the solution was filtered and the solids were washed with cold ACN. The target product was obtained as a white solid (7.6 g, 70%). $^{31}$P NMR (202.4 MHz, toluene-d$_8$): 142.5 and 140.9 (100%).

The unsymmetric bisphosphite (1Ia') was thus obtained, completely surprisingly and contrary to the prior art, in good yields and excellent purity even at low temperatures.

Purification of the Ligand (1Ia'):

As well as the suspending of the ligand in various solvents (see example above), it is also possible to purify the ligand by means of recrystallization. This recrystallization was effected to WO 2012095255. Rather than o-xylene, it is also possible to use toluene for recrystallization in an analogous manner.

Inventive Synthesis of the Ligand (1Ia")—General Reaction Equation

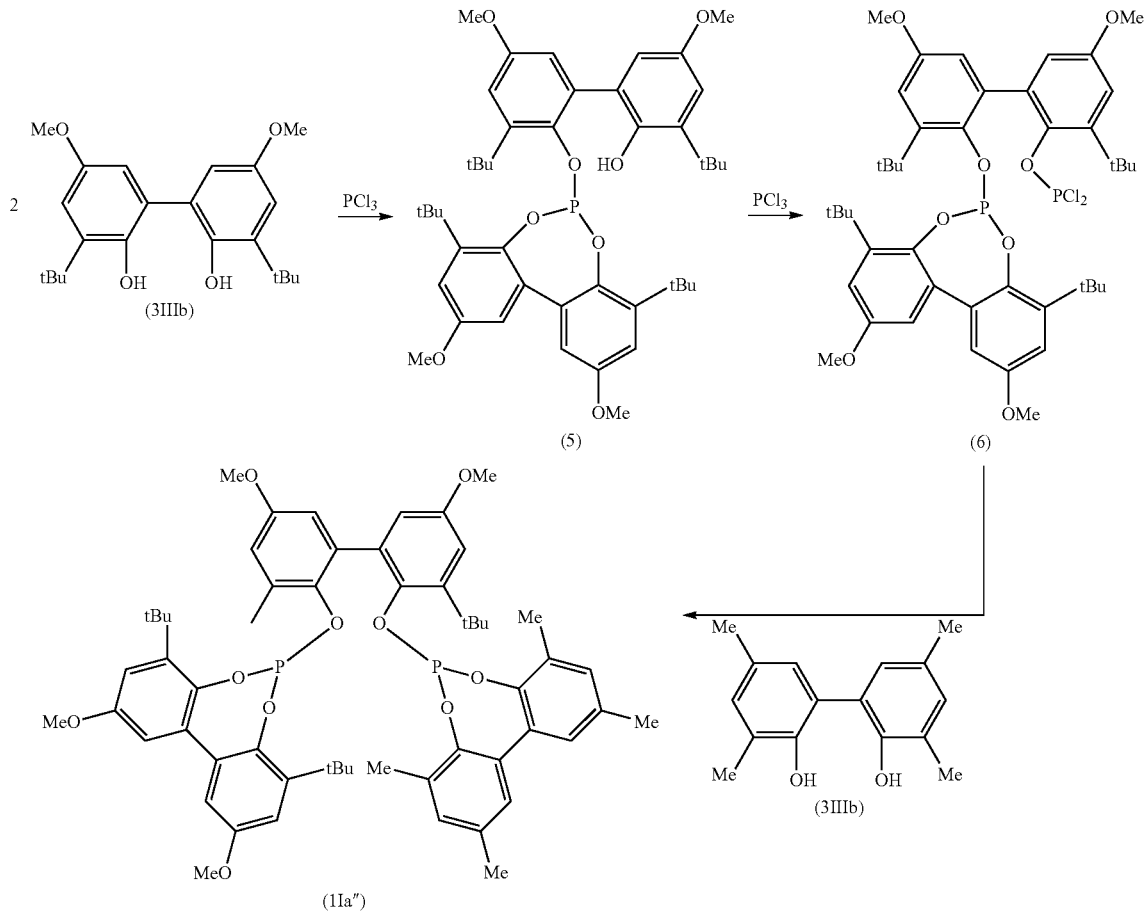

Synthesis of the Phosphite (5)

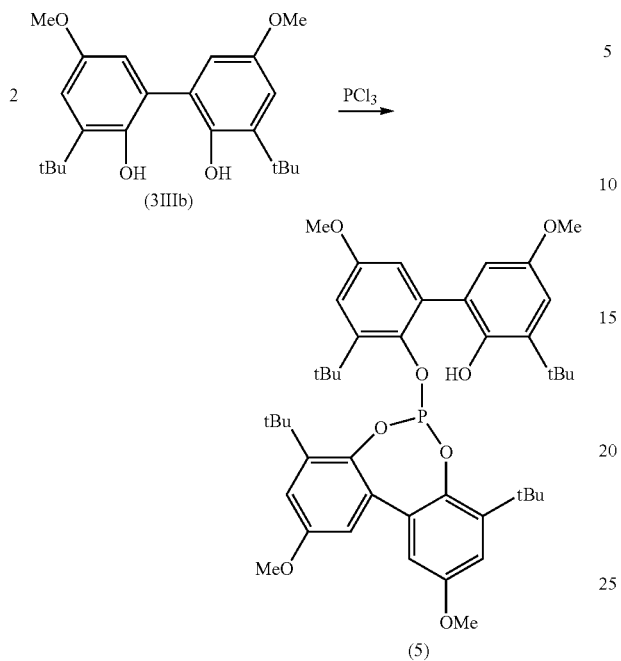

A secured 1000 ml Schlenk is initially charged with 400 ml of dried toluene, 8.9 ml (0.1 mol) of phosphorus trichloride are added by means of a syringe and the mixture is cooled to 0° C. 71.6 g (0.2 mol) of 3,3'-di-tert-butyl-2,2'-dihydroxy-5,5'-dimethoxybiphenyl are weighed into a 500 ml Schlenk and dissolved in 325 ml of dried toluene and 49 ml (0.35 mol) of dried triethylamine.

Then the biphenol/Et$_3$N/toluene suspension is added dropwise within 2.5 h to the PCl$_3$/toluene solution cooled to 0° C. and left to react at RT overnight.

The next morning, the solids formed were filtered off and washed repeatedly with dried toluene, and the filtrate was concentrated to dryness. In order to obtain a white solid, ACN was used for further washes. The target product was thus obtained in 79.5% yield (59.1 g).

Synthesis of the Diorganophosphite Dichlorophosphite (6)

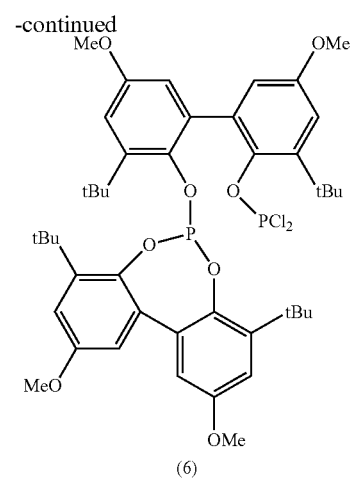

42 g (0.056 mol) of the phosphite (5) are weighed into a secured 250 ml Schlenk, and 275 ml of dried toluene and 17 ml (0.168 mol) of dried triethylamine are added while stirring.

A second 1000 ml Schlenk was first initially charged with 200 ml of dried toluene and then 14.76 ml (0.169 mol) of phosphorus trichloride were added. Subsequently, while stirring vigorously, the above-prepared phosphite/amine/toluene solution was added dropwise to the phosphorus trichloride/toluene solution at RT within 30 minutes. On completion of addition, the reaction mixture was heated to 80° C. for 6 h and allowed to come to RT overnight.

The next morning, the mixture was filtered, the solids were washed with 50 ml of dried toluene, and the filtrate was concentrated to dryness. The product was obtained in 89% yield (45.6 g).

Inventive Synthesis of the Ligand (1Ia")

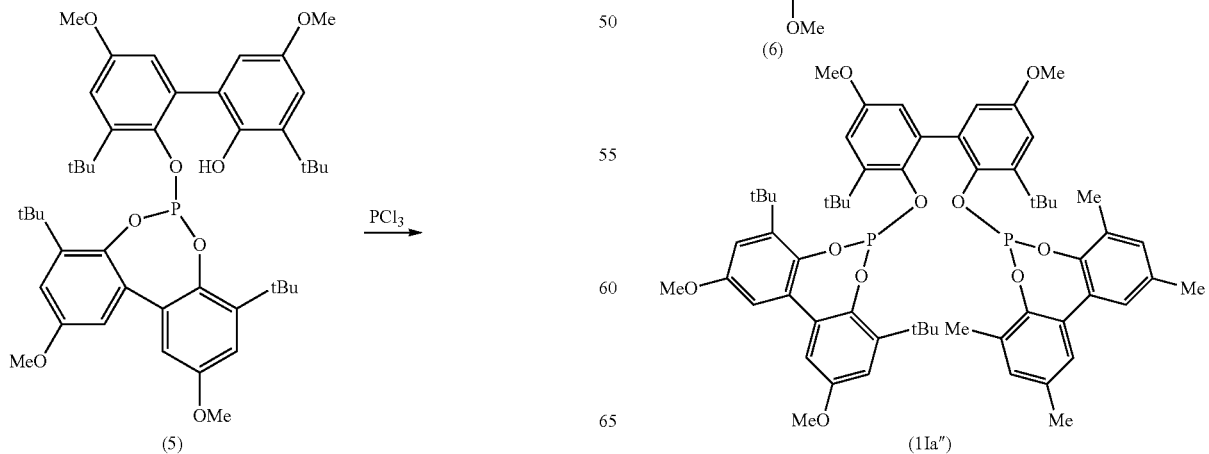

In a glovebox, 3.08 g (0.0036 mol) of diorganophosphite dichlorophosphite (6) were weighed into a secured 100 ml Schlenk and then dissolved in 35 ml of dried toluene.

In a second secured 250 ml Schlenk, 0.872 g (0.0036 mol) of 2,2'-bis(3,5-dimethylphenol) and 1.09 g (0.01 mol) of dried triethylamine were dissolved in 35 ml of toluene.

Then the diorganophosphite dichlorophosphite (6) was slowly and continuously added dropwise at RT to the biphenyl-triethylamine solution while stirring vigorously. Subsequently, the reaction mixture was stirred overnight.

For workup, the solids formed were filtered the next morning and washed twice with 5 ml of dried toluene. The resulting filtrate was then concentrated to dryness. The target product was obtained as a white solid (2.59 g; 71%).

Procedure for the Hydroformylation Experiments
Experiment Description—General

The experiments were conducted in 100 ml autoclaves from Parr Instruments. The autoclaves are equipped with an electric heater. The pressure is kept constant by means of mass flow meters and pressure regulators. During the experiment duration, a syringe pump can be used to inject an exactly defined amount of reactant under reaction conditions. Capillary lines and HPLC valves can be used to take samples during the experiment duration, and these can be analysed both by means of GC analysis and by means of LC-MS analysis.

Inventive Results of the Testing of the Various Ligand Mixtures of Ligands (1Ia') and (1Ia") in the Hydroformylation[a]:

The two bisphosphites (1Ia') and (1Ia") were mixed manually before use in the hydroformylation reaction.

Inventive Results—Substrate Variation

Example 1

In a 100 ml autoclave from Parr Instruments, 5.3 g of propene were hydroformylated at 120° C. and 30 bar. As the precursor, 0.0054 g Rh(acac)(CO)$_2$ was initially charged in 43.89 g of toluene. As the ligand, 0.0701 g of ligand (1Ia') was used in the catalyst mixture solution. 0.0372 g of the compound (7) was added as the organic amine, and 0.5016 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. 89.6 mol % butanal, 7.9 mol % 2-methylpropanal and 2.3 mol % propane were formed. The regioselectivity for n-butanal is 92.0%.

Example 2

In a 100 ml autoclave from Parr Instruments, 5.6 g of cis-2-butene were hydroformylated at 120° C. and 20 bar. As the precursor, 0.0056 g Rh(acac)(CO)$_2$ was initially charged in 48.8 g of toluene. As the ligand, 0.0779 g of ligand (1Ia') was used in the catalyst mixture solution. 0.0416 g of the compound (7) was added as the organic amine, and 0.5760 g of TIPB as the GC standard. The reactant was metered in after attainment of the reaction temperature envisaged. During the reaction, the pressure was kept constant via synthesis gas regulation with a mass flow meter. Samples were taken from

TABLE 4

| No. | Ligands | Content of ligands | Ratio of the ligands in [%][e] | Pentanal selectivity in mol [%][b] | Yield in [%][b] |
|---|---|---|---|---|---|
| 1 | ligand (1Ia') | 100% | L1Ia': 100% | 94.0[c] | 92.9[c] |
| 2 | ligand (1Ia") | 100% | L1Ia": 100% | 53.2 | 76.2 |
| 3* | ligand (1Ia') + ligand (1Ia") | L1Ia':L1Ia":Rh 2.3:2.2:1 | L1Ia': 51% + L1Ia": 49% | 79.6 | 93.8 |
| 4* | ligand (1Ia') + ligand (1Ia") | L1Ia':L1Ia":Rh 3.3:1.3:1 | L1Ia': 72% + L1Ia": 28% | 80.5 | 93.8 |
| 5* | ligand (1Ia') + ligand (1Ia") | L1Ia':L1Ia":Rh 1.2:2.8:1 | L1Ia': 30% + L1Ia": 70% | 79.6 | 91.0 |

A comparison of the various ligand mixtures of the unsymmetric ligands (1Ia') and (1Ia") (Table 4, entries 4-6) with the hydroformylation result for the pure ligand (1Ia") (Table 4, entry 2) shows that the mixtures have good pentanal selectivities and yields which are much higher than those for the pure ligand (1Ia") (Table 4, entries 2 and 3-5).

These good yields and selectivities of unsymmetric bisphosphites are completely surprising and contrary to the prior art, in which bisphosphites of unsymmetric structure, when used as a ligand in transition metal-catalysed hydroformylation, have much lower reactivities and lower n-regioselectivity (see Rhodium-catalyzed Hydroformylation, ed. by P. W. N. M. van Leeuwen and C. Claver, Kluwer Academic Publishers 2006, AA Dordrecht, NL, pages 45-46). In addition, a further unsymmetric bisphosphite produced a much higher pentanal selectivity than the pure ligand (1Ia").

It was thus shown that, in hydroformylation reactions, it is also possible to use ligand mixtures of unsymmetric bisphosphites which achieve the technical object.

the reaction mixture after 20 hours. 80.0 mol % pentanal, 5.2 mol % 2-methylbutanal and 3.7 mol % n-butane were formed. The regioselectivity for n-pentanal is 94.0%.

Example 3

In a 100 ml autoclave from Parr Instruments, 6.3 g of isobutene were hydroformylated at 120° C. and 20 bar. As the precursor, 0.0046 g Rh(acac)(CO)$_2$ was initially charged in 39.8 g of toluene. As the ligand, 0.0636 g of ligand (1Ia') was used in the catalyst mixture solution. 0.0339 g of the compound (7) was added as the organic amine, and 0.4701 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. 72.9 mol % 3-methylbutanal, 0.1 mol % pivalaldehyde and 4.4 mol % isobutane were formed.

Example 4

In a 100 ml autoclave from Parr Instruments, 6.7 g of a C-4 mixture having the following composition: 2.9 mol % isobutane, 9.9 mol % n-butane, 28.7 mol % 1-butene, 43.5 mol % isobutene, 14.6 mol % 2-butenes and 0.2 mol % 1,3-butadiene were hydroformylated at 120° C. and 20 bar. As the precursor, 0.0049 g Rh(acac)(CO)$_2$ was initially charged in 42.38 g of toluene. As the ligand, 0.0697 g of ligand (1Ia') was used in the catalyst mixture solution. 0.0374 g of the compound (7) was added as the organic amine, and 0.5069 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 32.86% 3-methylbutanal (isobutene conversion 75.6 mol %), 39.0 mol % n-pentanal and 1.8 mol % 2-methylbutanal (butenes conversion 76.5 mol %, regioselectivity for n-pentanal 95.6%). As hydrogenation products, 4.7 mol % isobutane and 11.3 mol % n-butane were found in the output.

Example 5

In a 100 ml autoclave from Parr Instruments, 6.5 g of a C-4 mixture having the following composition: 5.9 mol % isobutane, 15.6 mol % n-butane, 52.9 mol % 1-butene, 0.1 mol % isobutene, 24.8 mol % 2-butenes and 0.5 mol % 1,3-butadiene were hydroformylated at 120° C. and 20 bar. As the precursor, 0.0052 g Rh(acac)(CO)$_2$ was initially charged in 45.05 g of toluene. As the ligand, 0.0727 g of ligand (1Ia') was used in the catalyst mixture solution. 0.0377 g of the compound (7) was added as the organic amine, and 0.5314 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 0.14 mol % 3-methylbutanal, 69.5 mol % n-pentanal and 3.67 mol % 2-methylbutanal (butenes conversion 94.2 mol %, regioselectivity for n-pentanal 96.5%). As hydrogenation products, 5.64 mol % isobutane and 18.55 mol % n-butane were found in the output.

Example 6

In a 100 ml autoclave from Parr Instruments, 7.0 g of a C-4 mixture having the following composition: the reactant comprises 5.9 mol % isobutane, 22.1 mol % n-butane, 45.5 mol % 1-butene, 2.1 mol % isobutene, 17.1 mol % 2-butenes and 0.2 mol % 1,3-butadiene were hydroformylated at 120° C. and 20 bar. As the precursor, 0.0047 g Rh(acac)(CO)$_2$ was initially charged in 40.81 g of toluene. As the ligand, 0.0659 g of ligand (1Ia') was used in the catalyst mixture solution. 0.0342 g of the compound (7) was added as the organic amine, and 0.4814 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 1.5 mol % 3-methylbutanal (isobutene conversion 71.6 mol %), 61.9 mol % n-pentanal and 2.9 mol % 2-methylbutanal (butenes conversion 93.3 mol %, regioselectivity for n-pentanal 95.5%). As hydrogenation products, 5.3 mol % isobutane and 23.4 mol % n-butane were found in the output.

Example 7

In a 100 ml autoclave from Parr Instruments, 7.1 g of a C-4 mixture having the following composition: 3.5 mol % isobutane, 13.0 mol % n-butane, 47.3 mol % 1-butene, 13.9 mol % isobutene, 21.6 mol % 2-butenes and 0.4 mol % 1,3-butadiene were hydroformylated at 120° C. and 20 bar. As the precursor, 0.0048 g Rh(acac)(CO)$_2$ was initially charged in 43.88 g of toluene. As the ligand, 0.0680 g of ligand (1Ia') was used in the catalyst mixture solution. 0.0363 g of the compound (7) was added as the organic amine, and 0.5092 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 10.1 mol % 3-methylbutanal (isobutene conversion 72.8 mol %), 63.2 mol % n-pentanal and 3.2 mol % 2-methylbutanal (butenes conversion 96.3 mol %, regioselectivity for n-pentanal 95.2%). As hydrogenation products, 3.5 mol % isobutane and 15.1 mol % n-butane were found in the output.

Example 8

In a 100 ml autoclave from Parr Instruments, 5.8 g of a C-4 mixture having the following composition: 0.1 mol % isobutane, 27.6 mol % n-butane, 27.9 mol % 1-butene, 0.1 mol % isobutene and 44.0 mol % 2-butenes were hydroformylated at 120° C. and 20 bar. As the precursor, 0.0051 g Rh(acac)(CO)$_2$ was initially charged in 43.77 g of toluene. As the ligand, 0.0699 g of ligand (1Ia') was used in the catalyst mixture solution. 0.0373 g of the compound (7) was added as the organic amine, and 0.5166 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 59.9 mol % n-pentanal and 3.3 mol % 2-methylbutanal (butenes conversion 91.7 mol %, regioselectivity for n-pentanal 94.7%). As hydrogenation products, 0.1 mol % isobutane and 31.7 mol % n-butane were found in the output.

Example 9

In a 100 ml autoclave from Parr Instruments, 6.0 g of a C-4 mixture having the following composition: 63.6 mol % n-butane, 1.0 mol % 1-butene and 35.8 mol % 2-butenes were hydroformylated at 120° C. and 20 bar. As the precursor, 0.0041 g Rh(acac)(CO)$_2$ was initially charged in 35.88 g of toluene. As the ligand, 0.0573 g of ligand (1Ia') was used in the catalyst mixture solution. 0.0306 g of the compound (7) was added as the organic amine, and 0.4235 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 29.7 mol % n-pentanal and 1.9 mol % 2-methylbutanal (butenes conversion 85.3 mol %, regioselectivity for n-pentanal 94.0%).

Example 10

In a 100 ml autoclave from Parr Instruments, 5.0 g of n-octenes were hydroformylated at 120° C. and 20 bar. As the precursor, 0.0049 g Rh(acac)(CO)$_2$ was initially charged in 41.29 g of toluene. As the ligand, 0.0669 g of ligand (1Ia') was used in the catalyst mixture solution. 0.0378 g of the compound (7) was added as the organic amine, and 0.5030 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 54.2 mol % aldehydes (regioselectivity for n-nonanal 90.9%). As hydrogenation products, 3.9 mol % n-octane and 3.2% nonanol were found in the output.

Example 11

In a 100 ml autoclave from Parr Instruments, 7.0 g of 1,3-butadiene were hydroformylated at 120° C. and 20 bar. As the precursor, 0.0054 g Rh(acac)(CO)$_2$ was initially charged in 46.82 g of toluene. As the ligand, 0.0770 g of ligand (1Ia') was used in the catalyst mixture solution. 0.0413 g of the compound (7) was added as the organic amine, and 0.5599 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 0.2 mol % n-butane, 11.3% n-butenes, 12.9% aldehydes and 11.5 mol % 4-vinylcyclohexene. The total conversion of 1,3-butadiene is 37.2%.

Example 12

In a 100 ml autoclave from Parr Instruments, 5.6 g of methyl oleate were hydroformylated at 120° C. and 20 bar. As the precursor, 0.0052 g Rh(acac)(CO)$_2$ was initially charged in 44.06 g of toluene. As the ligand, 0.0689 g of ligand (1Ia') was used in the catalyst mixture solution. 0.0375 g of the compound (7) was added as the organic amine, and 0.5260 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. From $^1$H and $^{13}$C NMR spectra, an aldehyde yield of 49.5 mol % was calculated. The regioselectivity for terminal aldehydes is 20.6 mol %. The double bond content is 35.9 mol %.

Example 13

In a 100 ml autoclave from Parr Instruments, 6.9 g of a hydrocarbon mixture from catalytically operated cracking plants having the following composition: 1.5 mol % propane, 0.8 mol % propene, 28.1 mol % isobutane, 8.1 mol % n-butane, 16.4 mol % 1-butene, 16.9 mol % isobutene, 28.2 mol % 2-butenes, 0.5 mol % 1,3-butadiene and fractions of C5 olefins and hydrocarbons were hydroformylated at 120° C. and 20 bar. As the precursor, 0.0048 g Rh(acac)(CO)$_2$ was initially charged in 43.39 g of toluene. As the ligand, 0.0672 g of ligand (1Ia') was used in the catalyst mixture solution. 0.0359 g of the compound (7) was added as the organic amine, and 0.5035 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours.

The output comprises 1.3 mol % propane, 0.7 mol % butanal, 27.5 mol % isobutane, 9.6 mol % n-butane, 13.1 mol % 3-methylbutanal (77.4% isobutene conversion), 39.1 mol % pentanal, 2.1 mol % 2-methylbutanal (n-butenes conversion 96.9%, regioselectivity for n-pentanal 95.0%).

Example 14

In a 100 ml autoclave from Parr Instruments, 1.8 g of ethene were hydroformylated at 120° C. and 50 bar. As the precursor, 0.0050 g Rh(acac)(CO)$_2$ was initially charged in 42.68 g of toluene. As the ligand, 0.0668 g of ligand (1Ia') was used in the catalyst mixture solution. 0.0363 g of the compound (7) was added as the organic amine, and 0.5095 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The conversion to propanal is 98.7%.

For the experiments which follow, the ligand (1Ia") and combinations of the two unsymmetric ligands (1Ia') and (1Ia") were examined.

Example 15

In a 100 ml autoclave from Parr Instruments, 6.0 g of cis-2-butene were hydroformylated at 120° C. and 20 bar. As the precursor, 0.0049 g Rh(acac)(CO)$_2$ was initially charged in 44.38 g of toluene. As the ligand, 0.0783 g of ligand (1Ia") was used in the catalyst mixture solution. 0.0392 g of the compound (7) was added as the organic amine, and 0.4981 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours. 53.2 mol % pentanal, 16.6 mol % 2-methylbutanal and 3.19 mol % n-butane were formed. The regioselectivity for n-pentanal is 76.2%.

Example 16

In a 100 ml autoclave from Parr Instruments, 5.9 g of cis-2-butene were hydroformylated at 120° C. and 20 bar. As the precursor, 0.0045 g Rh(acac)(CO)$_2$ was initially charged in 43.5 g of toluene. As ligand, 0.036 g of ligand (1Ia') and 0.0383 g of ligand (1Ia") (molar L1Ia':L1Ia":Rh ratio=2.3:2.2:1) were used in the catalyst mixture solution. 0.0374 g of the compound (7) was added as the organic amine, and 0.5096 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours. 79.6 mol % pentanal, 5.27 mol % 2-methylbutanal and 3.65 mol % n-butane were formed. The regioselectivity for n-pentanal is 93.8%.

Example 17

In a 100 ml autoclave from Parr Instruments, 6.3 g of cis-2-butene were hydroformylated at 120° C. and 20 bar. As the precursor, 0.0049 g Rh(acac)(CO)$_2$ was initially charged in 45.0 g of toluene. As ligand, 0.0568 g of ligand (1Ia') and 0.0249 g of ligand (1Ia") (molar L1Ia':L1Ia":Rh ratio=3.3:1.3:1) were used in the catalyst mixture solution. 0.0376 g of the compound (7) was added as the organic amine, and 0.5103 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours. 80.5 mol % pentanal, 5.29 mol % 2-methylbutanal and 3.08 mol % n-butane were formed. The regioselectivity for n-pentanal is 93.8%.

Example 18

In a 100 ml autoclave from Parr Instruments, 5.6 g of cis-2-butene were hydroformylated at 120° C. and 20 bar. As the precursor, 0.0054 g Rh(acac)(CO)$_2$ was initially charged in 45.6 g of toluene. As ligand, 0.0215 g of ligand (1Ia') and 0.0587 g of ligand (1Ia") (molar L1Ia':L1Ia":Rh ratio=1.2:2.8:1) were used in the catalyst mixture solution. 0.0364 g of the compound (7) was added as the organic amine, and 0.5073 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours. 79.6 mol % pentanal, 7.9 mol % 2-methylbutanal and 3.63 mol % n-butane were formed. The regioselectivity for n-pentanal is 91.0%.

The invention claimed is:

1. A mixture comprising the unsymmetric compounds (Ia') and (Ia"):

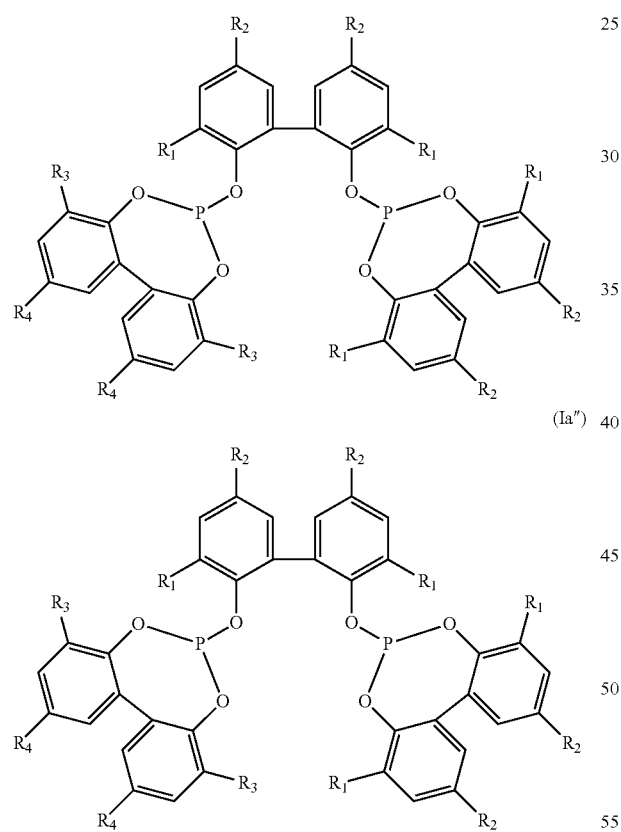

wherein
each R1, independently, is selected from the group consisting of -Me, -tBu, and —OMe;
each R2, independently, is selected from the group consisting of -Me, -tBu, and —OMe;
each R3, independently, is selected from the group consisting of -Me, -tBu, and —OMe;
each R4, independently, is selected from the group consisting of -Me, -tBu, and —OMe;
and P can enter into further bonds,
and the compounds (Ia') and (Ia") are not identical.

2. The mixture according to claim 1,
wherein a content of compound (Ia') is from 99.5 to 0.5 mol %, and a content of compound (Ia") is from 0.5 to 99.5 mol %.

3. The mixture according to claim 1,
further comprising the bisphosphites of the formulae (Ib') and (Ib"):

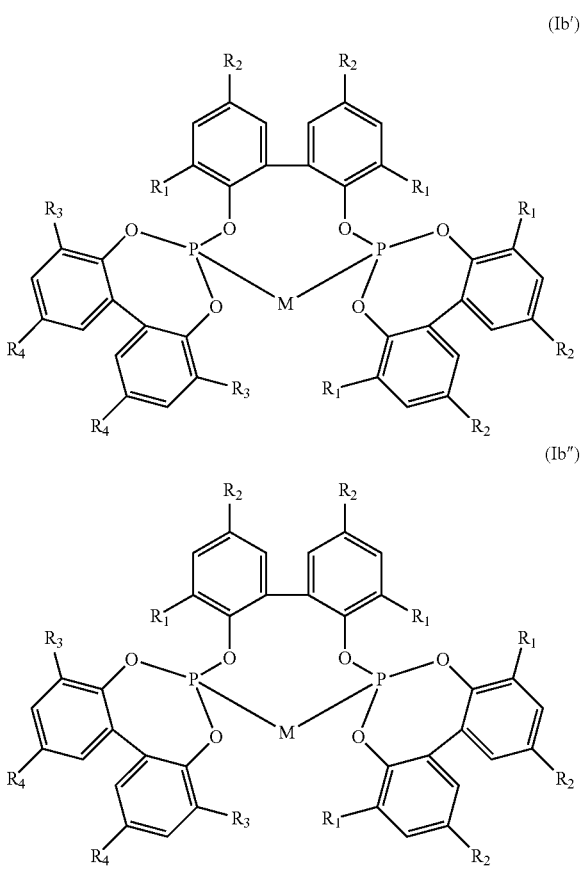

wherein M is selected from Fe, Ru, Os, Co, Rh, Ir, Ni, Pd, and Pt,
and M can enter into additional bonds,
and the compounds (Ib') and (Ib") are not identical.

4. The mixture according to claim 1,
further comprising the compounds of the formulae (Ic') and (Ic"):

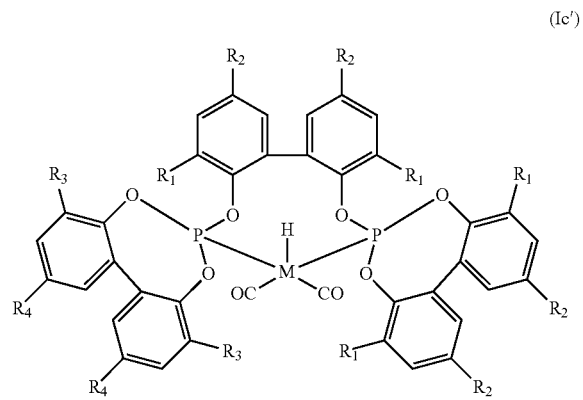

-continued (Ic")

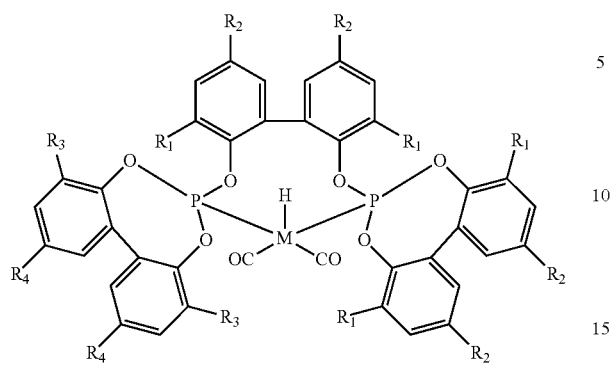

wherein M is selected from Fe, Ru, Os, Co, Rh, Ir, Ni, Pd, and Pt,
and the compounds (Ic') and (Ic") are not identical.

5. The mixture according to claim 4, which additionally comprises at least one compound (Ia') or (Ia") not bonded to M.

6. The mixture according to claim 3, wherein M is Rh.

7. The mixture according to claim 1, wherein, for each of formula Ia' and Ia", R1 is -Me, and R3 is not -Me.

8. The mixture according to claim 1, wherein, for each of formula Ia' and Ia", R2 is -Me, and R4 is not -Me.

9. The mixture according to claim 1, wherein, for each of formula Ia' and Ia", R1 and R2 are each -Me.

10. The mixture according to claim 1, wherein R1 is -tBu, and R3 is not -tBu.

11. The mixture according to claim 1, wherein R2 is —OMe, and R4 is not —OMe.

12. A composition, comprising:
a mixture of claim 1; and
a further component selected from the group consisting of bases, organic amines, epoxides, buffer solutions, and ion exchangers.

13. The composition according to claim 12, wherein the organic amine has a 2,2,6,6-tetramethylpiperidine unit.

14. A process for preparing a mixture of claim 1, comprising:
a) oxidative coupling of (IIa) to (IIIa):

(IIa)

(IIIa)

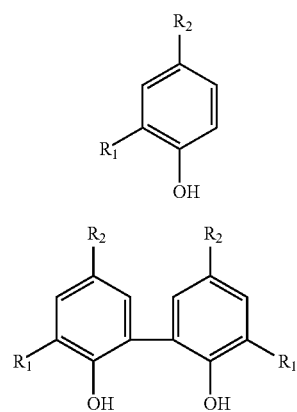

b) oxidative coupling of (IIb) to (IIIb):

(IIb)

(IIIb)

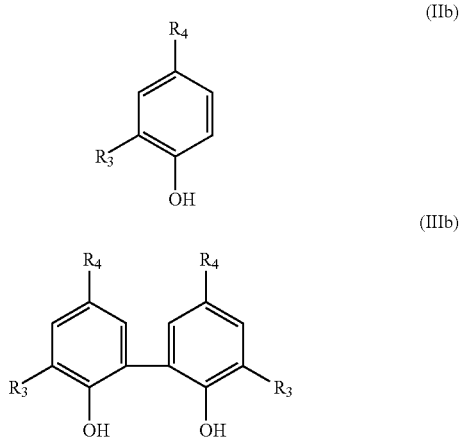

c) reacting the product (IIIa) from a) with PCl$_3$ forming (IVa):

(IIIa)

(IVa)

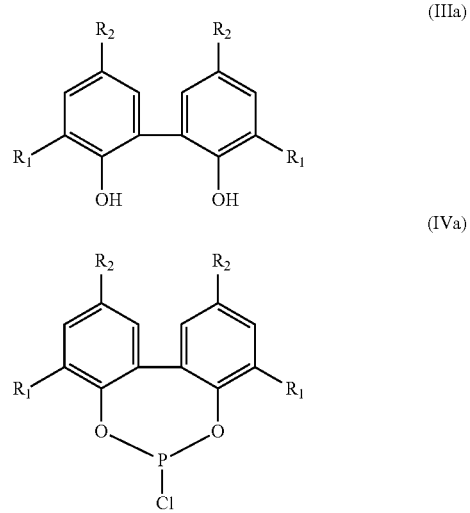

d) reacting the product from b) with the product from c) to obtain a bisphosphite,
e) repeating a) to d), where the R1 to R4 radicals are selected such that they are not all identical to the first run, and
f) mixing the compounds from the first and second runs.

15. The process according to claim 14, additionally comprising:
g) reacting with M to obtain (Ic') and (Ic"), where M is selected from the group consisting of Fe, Ru, Os, Co, Rh, Ir, Ni, Pd, and Pt:

(Ic')

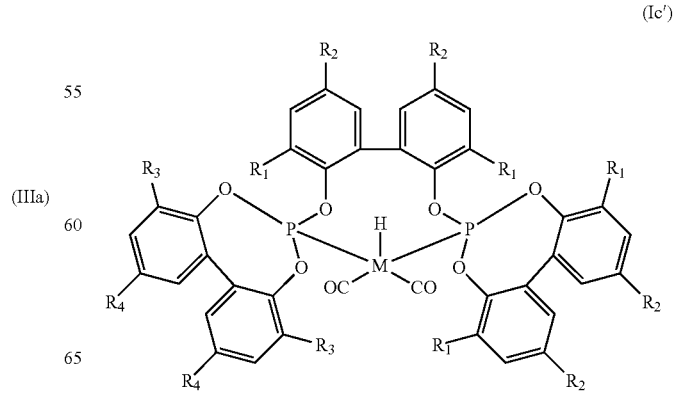

-continued
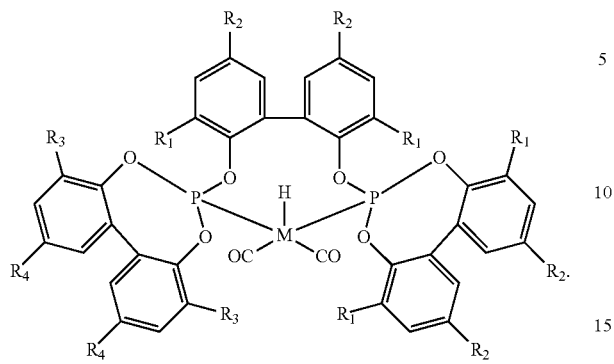
(Ic″)
16. The mixture according to claim 1, wherein the mixture is suitable as a catalyst in a hydroformylation reaction of unsaturated compounds and mixtures thereof.
* * * * *